United States Patent [19]
Elvin et al.

[11] Patent Number: 6,034,296
[45] Date of Patent: Mar. 7, 2000

[54] IMPLANTABLE BONE STRAIN TELEMETRY SENSING SYSTEM AND METHOD

[76] Inventors: Niell Elvin; Alex Elvin, both of 1110 W. Gate Apartments 550 Memorial Dr., Cambridge, Mass. 02139; Myron Spector, 921 Seaver St., Brookline, Mass. 02146

[21] Appl. No.: 08/984,957

[22] Filed: Dec. 4, 1997

Related U.S. Application Data

[60] Provisional application No. 60/040,325, Mar. 11, 1997.
[51] Int. Cl.$^7$ ............................... A61F 2/28; A61B 17/68
[52] U.S. Cl. ........................... 623/16; 600/302; 128/903; 606/60
[58] Field of Search ....................... 623/16, 24; 128/903; 600/302; 73/781

[56] References Cited

U.S. PATENT DOCUMENTS

| | | |
|---|---|---|
| 3,853,117 | 12/1974 | Murr . |
| 4,080,653 | 3/1978 | Barnes, Jr. et al. . |
| 4,281,667 | 8/1981 | Cosman . |
| 4,407,296 | 10/1983 | Anderson . |
| 4,494,411 | 1/1985 | Koschke et al. . |
| 4,519,401 | 5/1985 | Ko et al. . |
| 4,781,181 | 11/1988 | Tanguy . |
| 5,125,408 | 6/1992 | Basser . |
| 5,188,109 | 2/1993 | Saito ........................................ 128/635 |
| 5,342,362 | 8/1994 | Kenyon et al. . |
| 5,373,852 | 12/1994 | Harrison et al. . |
| 5,456,724 | 10/1995 | Yen et al. . |
| 5,531,787 | 7/1996 | Lesinski et al. . |
| 5,695,496 | 12/1997 | Orsak et al. .............................. 606/54 |

FOREIGN PATENT DOCUMENTS

93/06789  4/1993  WIPO .

OTHER PUBLICATIONS

Kilvington et al., Engineering in Medicine, vol. 10, No. 4, pp. 175–187, 1981.

*Primary Examiner*—David H. Willse

[57] ABSTRACT

An implantable self-powered sensing system for a bone fixation device, which includes a self-powered strain sensor mountable on or in a bone fixation device, is disclosed. The sensor is capable of measuring strain in the bone fixation device by generating a strain signal in response to stresses produced thereupon. The system also includes a telemetry unit powered by the generated strain signal and in communication with the sensor. The telemetry unit is activated by the sensor when the strain signal reaches a predetermined value and then transmits the strain signal from the sensor to an external receiver. The sensing system can also include a buffer unit in communication with the sensor and the telemetry unit for collecting and storing the strain signals for transmission by the telemetry unit as a cumulative strain measurement. The method of monitoring healing in a bone and measuring strain in a bone fixation device using the sensing system of the present invention includes the steps of subjecting a patient to a predetermined set of dynamic exercises which vary stresses exerted on the bone fixation device and tests the integrity of the bone fixation device and then measuring the strain resulting from the stresses imposed upon the bone fixation device via the implanted self-powered sensor attached to the bone fixation device, which generates a charge in response to the stresses imposed on the bone fixation device, which then powers the implanted telemetry unit in order to transmit the charge generated by the sensor unit to an external receiver as a corresponding strain measurement signal.

7 Claims, 4 Drawing Sheets

IMPLANTABLE BONE STRAIN TELEMETRY SENSING SYSTEM AND METHOD

CROSS REFERENCE TO RELATED APPLICATIONS

This application claims the benefit of U.S. Provisional Application No. 60/040,325, filed Mar. 11, 1997.

STATEMENT REGARDING FEDERALLY SPONSORED RESEARCH OR DEVELOPMENT

N/A.

BACKGROUND OF THE INVENTION

The present invention relates to biomedical implants, and more particularly to an implantable telemetry sensor for monitoring bone fracture fixation devices.

Historically, radiography has been used to monitor fracture healing. This method gives only qualitative indications of the extent of healing and cannot be used for continuous everyday monitoring. Monitoring has also been performed with strain gauges used to make regular measurements in orthopedic implants so as to assess the quantitative characterization of the healing process. These efforts are directed towards reducing the number of mechanical implant failures and bone refracturing events. However, the powering of strain sensors has been a major obstacle. They have been powered by percutaneous leads that are potential infection sites, battery power which is dependent on battery longevity, and inductive powering which either complicates surgical procedures and/or requires large external power supplies. These methods are only suited for short-term laboratory testing and are impractical for long-term clinical use. Moreover, prior art sensors required relatively high power requirements and used from 500 mW of battery power to 5 watts of induced external power.

It would be desirable to provide a fracture healing assessment technique that is inexpensive and gives qualitative indications of the extent of healing. It would also be desirable to allow for monitoring of dangerous overloads during rehabilitation exercises or day-to-day living. Additionally, a desired device should be non-intrusive and compatible with existing surgical techniques.

SUMMARY OF THE INVENTION

The present invention overcomes the above disadvantages by providing an implantable self-powered sensing system for a bone fixation device, which includes a self-powered strain sensor mountable about a bone fixation device. The sensor is capable of monitoring and measuring strain in the bone fixation device by generating a charge in response to stresses applied thereupon. The system also includes a telemetry unit powered by the sensor. The telemetry unit is activated by the sensor when the generated charge reaches a predetermined value; the telemetry system then transmits a strain signal, corresponding to the charge, from the sensor to an external receiver. The sensing system can also include a buffer unit in communication with the sensor and the telemetry unit for collecting and storing the generated charge (i.e., the strain signals) for transmission by the telemetry unit as an average or cumulative strain measurement.

The method of monitoring and measuring strain and healing in a bone and bone fixation device using the sensing system of the present invention includes the steps of subjecting a patient to a predetermined set of exercises which vary stresses exerted on the bone fixation device and tests the integrity of the bone fixation device. Subsequently, the strain resulting from the stresses imposed upon the implanted self-powered sensor attached to the bone fixation device generates a charge in response to the stresses imposed on the bone fixation device, which then powers the implanted telemetry unit in order to transmit the charge generated by the sensor unit to an external receiver corresponding to the strain measurement signal.

The present invention provides for monitoring the extent of healing in a bone. The sensor system can be used to determine the soundness and integrity of the bone fixation device and the integrity of the attachment method. The present invention monitors the extent of healing and the condition of the bone fixation device by monitoring the fixation device itself. The present invention can ascertain the amount of strain in the bone fixation device and allows the determination of the stiffness and the strain in the bone for which the fixation device is intended.

BRIEF DESCRIPTION OF THE DRAWINGS

The invention will be more fully understood by reference to the following detailed description when considered in conjunction with the accompanying drawings, in which.

DETAILED DESCRIPTION OF THE INVENTION

Figure 1:
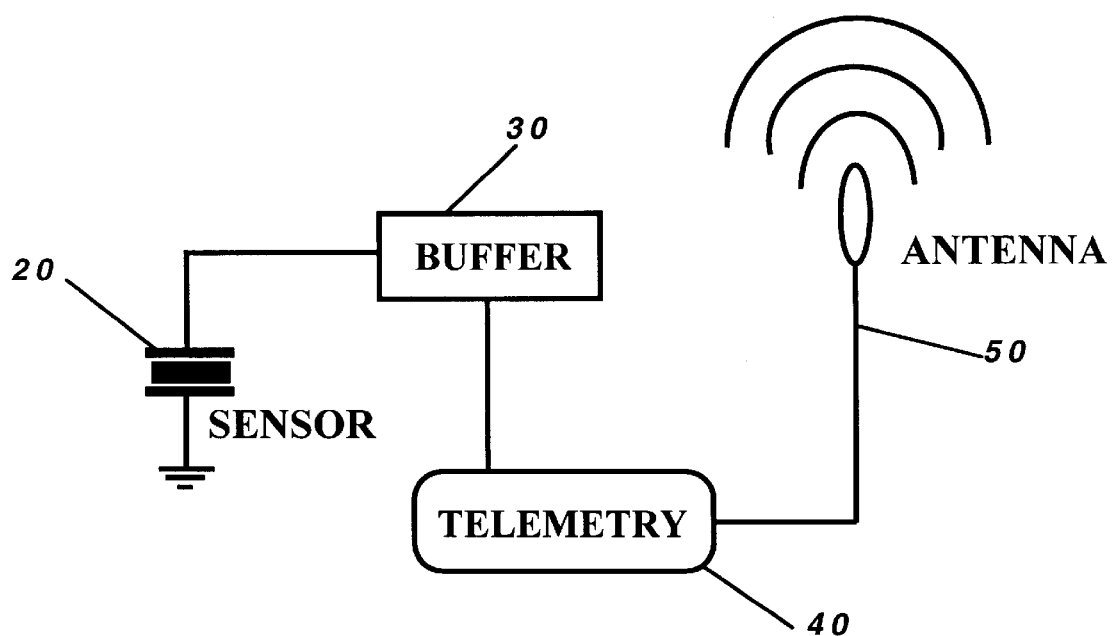
FIG. 1 is a schematic representation of the sensing system of the present invention.

FIG. 1 is an illustration of a sensing system in accordance with the present invention. The present invention claims priority from U.S. Provisional Application No. 60/040,325, which is hereby incorporated herein by reference as if set forth in full. The sensing system of the present invention is intended to be implanted in a patient's body on or in bone fixation devices, such as intramedullar nails, bone plates, or screws. For example, a patient who has fractured a long bone, might typically have an intramedullar nail surgically affixed within the bone to initiate and support the healing of the fractured bone. The sensing system of the present invention would be entirely affixed to the intramedullar nail in such a way as to sense the strain of the nail, i.e., the displacement of the device per unit distance, in response to the stress upon the nail, i.e., the applied force per unit area on the device, in order to determine the extent of healing in the bone and the integrity of the intramedullar nail. From the imposed stress and the measured strain, the stiffness can be calculated directly, i.e., stress divided by strain.

The sensing system can be implemented in several embodiments. One such system includes a sensor 20, for measuring strain on a bone fixation device, and from which stiffness can be calculated, a buffer unit 30 for collecting and storing the generated charges (i.e., strain signal measurements) from the sensor 20, and a telemetry unit 40 for transmitting strain measurement signals via an antenna 50 to an external receiver. Other embodiments can utilize either the sensor 20 itself with an external receiver acquiring the charge generated by sensor 20, or the sensor 20 can directly power the telemetry unit 40. The sensor system of the present invention is configured to be implanted into a patient's body affixed entirely on or in bone-fixation devices. The sensing system is self-powered; it does not require electrical batteries or any other means of internal or external power, such as powering by induction. Power generation is integral with the sensor 20. A sensor element generates power in the form of a charge, which is a function of the amount of strain in response to and corresponding to the stress put upon the fixation device and hence on the sensor element. Stress occurs upon a bone or bone fixation device when weight or force is put on a particular bone by movement of particular areas of a patient's body. For example, walking or exercise will put stress upon the bones of a person's legs. The charge generated by the sensor is typically collected and stored by the buffer unit 30. When a predetermined charge is accumulated by the buffer unit 30, then the telemetry unit 40 is activated. The telemetry unit 40 uses the collected charge to transmit a signal to an external receiver outside the body. When the charge falls below a preset amount, the telemetry unit will cease to transmit. This process continually repeats without any additional external power supply, making this system self-sensing and self-powered. In situations where continual direct sensing of strain is desired, the buffer unit 30 is not required and the telemetry unit 40 can directly send strain signals, i.e., amount of charge generated, from the sensor 20.

The sensing system can operate in one of two modes, direct or average. In the first mode, the amount of stress placed on a fracture fixation device is converted into a power signal corresponding to a strain measurement measured by the sensor 20 and transmitted via the telemetry unit 40 to an outside receiver. This is the direct sensing mode. In the second mode, the fixation device is loaded by a sequence of stresses. The strain measured by the sensor 20 results in charges being generated that are accumulated in the buffer unit 30 and a signal is then transmitted via the telemetry unit 40. This is the average sensing mode. The direct sensing mode uses only the sensor 20 and the telemetry unit 40, while the average sensing mode uses the sensor 20, the buffer unit 30, and the telemetry unit 40. In the direct sensing mode, every stress placed upon the fracture fixation device is converted into a signal and transmitted as a strain measurement. In contrast, the average sensing mode stores the charges generated by a number of strain cycles, which are in response to stresses placed upon the fracture fixation device, which is then sent as a cumulative sum by the telemetry unit 40 to an external receiver.

The sensing system automatically transmits strain measurements upon the occurrence of a predetermined amount of stress placed on a fixation device, thus, the system can warn of impending over-stress of the bone or bone fixation device. The sensing system transmits a signal corresponding to the strain measurements via wireless communications, thus not requiring leads or wires extending from the sensor, for example, to just below the skin or through the skin for transcutaneous communication. The entire sensor unit is mounted on a fracture fixation device and can be implanted either deeply in the body or close to the skin. The sensing system of the present invention can be mounted on any bone fixation device. FIGS. 2–6 illustrate embodiments of the present invention as used on bone fixation devices, such as an intramedullar nail and a bone plate.

Figure 2:
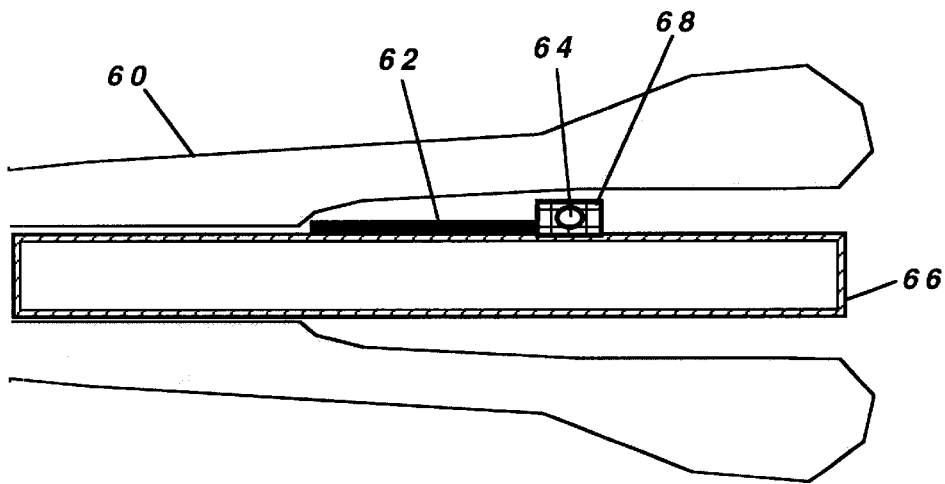
FIG. 2 is an illustration of an embodiment of the sensing system attached to a bone-fixation device.
Figure 3:
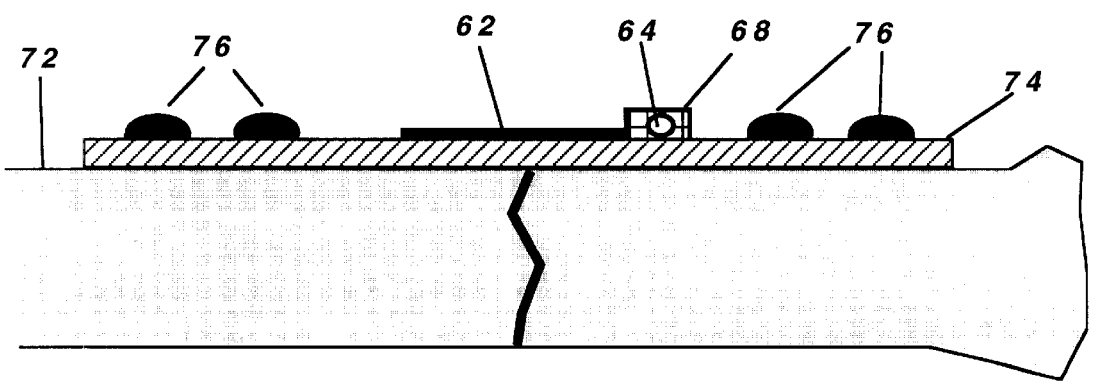
FIG. 3 is an illustration of another embodiment of the sensing system attached to a bone plate.

FIGS. 2 and 3 show examples of how the sensing system is mounted and used in relation to bone-fixation devices. In FIG. 2, an intramedullar nail 66 is used as a fixation device for a reamed bone 60. The sensing system is mounted entirely on the nail 66 as shown in FIG. 2. The sensor element 62 of the sensing system is positioned where it can measure strain in the fixation device from which the strain in the adjacent bone can be deduced in response to stress put upon the bone and/or bone fixation device. The buffer and telemetry units are shown in an encasement 68 as an integral circuit 64.

FIG. 3 depicts another embodiment of the sensor system affixed to a bone plate 74 used on a fractured bone 72. The sensor element 62 is attached to the bone plate 74, preferably proximate to the fracture site in the bone. The bone plate 74 is shown attached to the fractured bone 72 by use of plate screws 76. In this embodiment, sensor element 62 measures the stress put upon the bone plate 74, due to the weakness of the fractured bone 72 conveying any force applied to the bone 72 as an immediate stress upon the bone plate 74. As the bone heals and the mechanical effect of the fracture is less significant, the plate 74 will receive less stress and therefore less resulting strain upon it. Therefore, the extent of healing in the bone can be determined by monitoring the strain upon the bone fixation device.

Figure 4:
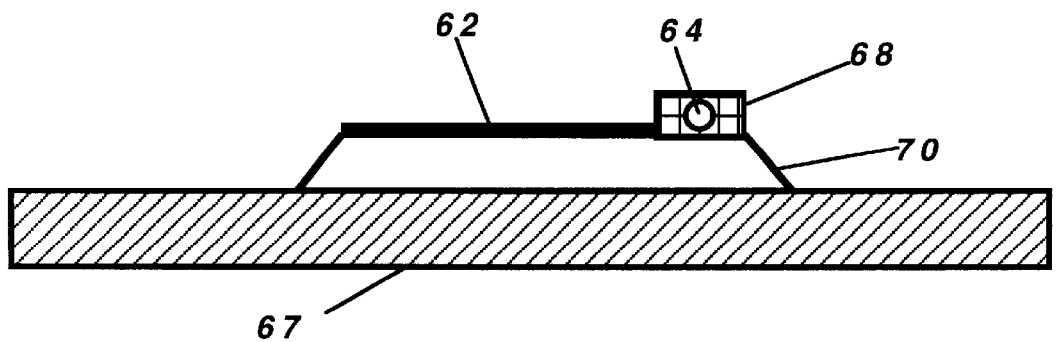
FIG. 4 is a detailed illustration of an embodiment of the sensing system as it is attached to a bone-fixation device.

FIG. 4 shows a more detailed view of the sensing system shown in FIG. 2 or FIG. 3. The sensing element 62 is shown attached to a fixation device 67 by a biocompatible and durable adhesive 70. The buffer and telemetry units are shown encased in a protective biocompatible encasement 68, which is also attached to sensing element 62 and the device 67 by way of the adhesive 70. The sensor element 62 and buffer and telemetry units are hermetically sealed and the buffer and telemetry circuitry 64 is surrounded by the protective encasement 68, which can be, for example, a titanium or ceramic encasement. The encased circuitry 64 is preferably placed where it will not be damaged or ruined during surgery or during the proceeding healing of the bone. One example of, the sensor element 62 is a piezoelectric material, but other power generating materials can be used.

Figure 5:
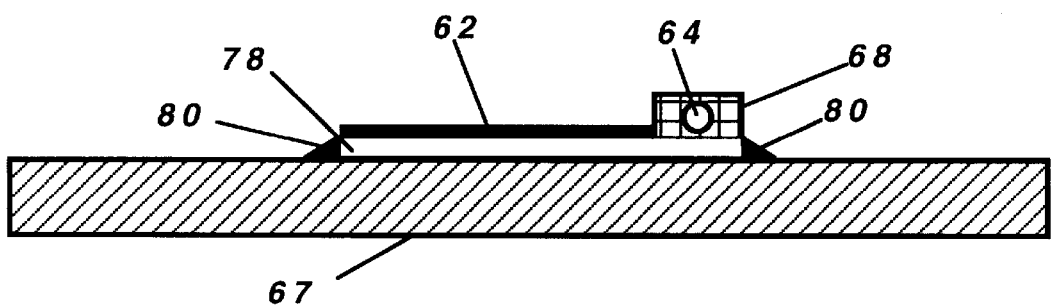
FIG. 5 is a detailed illustration of another embodiment of an attachment of the sensing system to a bone-fixation device.
Figure 6:
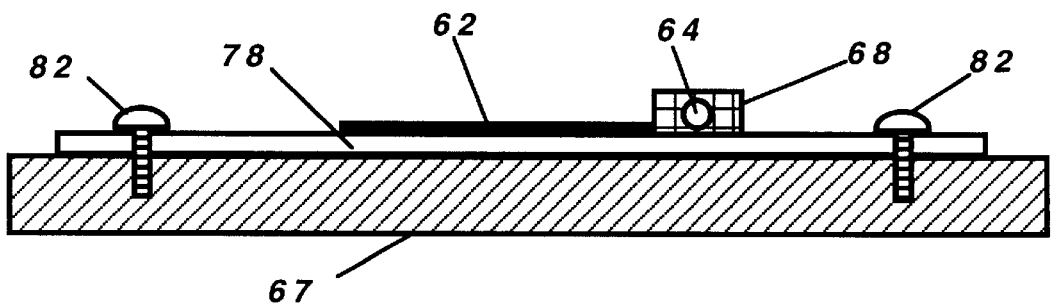
FIG. 6 is an illustration of another embodiment of the sensing system attached to a bone-fixation device.

FIGS. 5 and 6 show two additional embodiments of how a sensing system can be attached to a bone fixation device 67, such as a bone plate or intramedullar nail. In FIG. 5, sensing element 62 and circuitry 64 inside encasement 68 are attached to a bone-fixation device via a metal substrate 78. The metal substrate 78 and the sensing system are attached to the bone fixation device by fillet welds 80, in FIG. 5. The metal substrate 78 and sensing system are attached to the bone-fixation device by attachment screws 82, in FIG. 6. These attachment screws 82 can be the existing bone plate screws or can be specialized sensor attachment screws. The sensor can be attached inside or outside intramedullar nails.

After the sensing system is mounted on a fracture-fixation device and is implanted into the body of a patient, the sensor can then begin to monitor strain in the fracture fixation device. In a typical method of operation, a patient is subjected to a predetermined set of dynamic exercises and maneuvers during rehabilitation. These exercises put various stresses on the bone-fixation device from which the extent of healing and the integrity of the bone-fixation device can be determined. As the healing process progresses, the bone becomes stiffer and hence the measured strain on the fixation device decreases (i.e., the bone becomes more load bearing). The strain history is recorded and indicates the extent of healing. The strain sensor will indicate any increase in strains in the fixation device. Such increases in strain can be attributed to bone atrophication, malunion, or refracture. The sensor system detects the resulting strain on the bone fixation device from the dynamic exercises and then powers the telemetry unit. From the measured strain the stiffness of the bone, and hence the extent of healing, can be ascertained. The telemetry unit transmits to an external receiver outside the body, which then can record and analyze the strain signals. Periodic monitoring with the sensor system indicates the weight bearing ability of the fractured bone. The extent of healing in the bone and the permissible patient activity can then be inferred and deduced. In addition, the sensor system also allows for monitoring fixation device stability or bone atrophication. The sensor system can also indicate when it is appropriate and safe to remove the bone fixation device. Under normal healing conditions, analysis of the strain history will show a continuously decreasing strain. Based on an understanding of the strain history of the bone and medical experience, a surgeon can determine at which stage the fracture fixation device can be removed safely. Moreover, a patient can monitor the sensing system continuously during everyday activities, thus warning the patient when the fixation device is overloaded thereby aiding in preventing possible injury or failure of the device.

Figure 7:
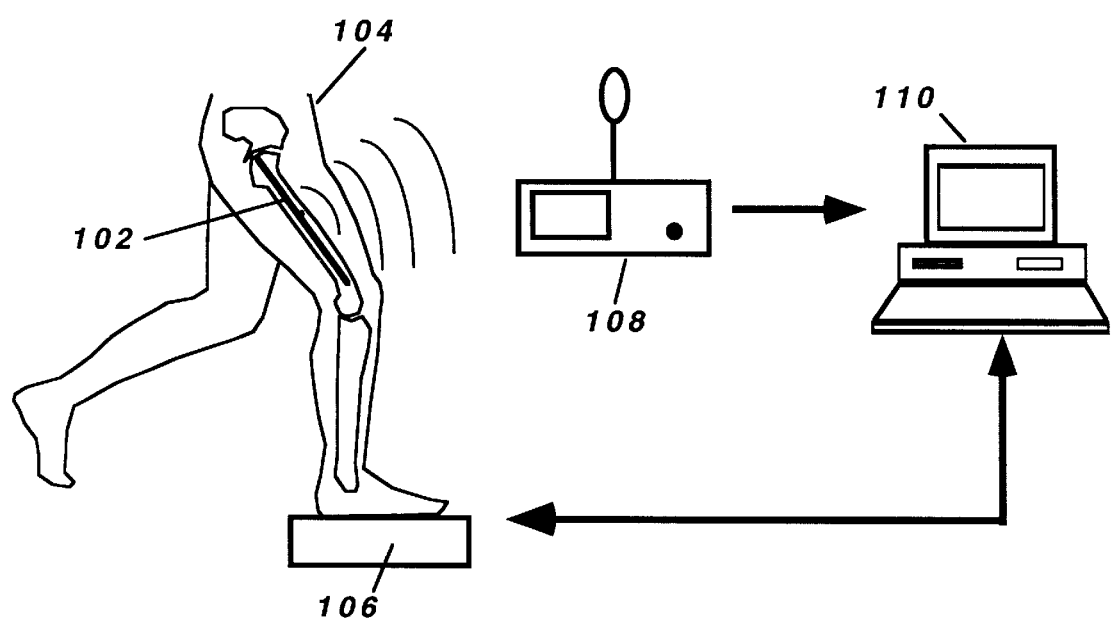
FIG. 7 is an illustration of an embodiment of the sensing system in use with external equipment.

FIG. 7 depicts an embodiment of using the present invention with external equipment. During the healing process of a fractured bone 100, a fracture fixation device 102 is typically monitored periodically at discrete points in time. The monitoring steps comprise subjecting a patient 104 to a predetermined and controlled set of rehabilitative exercises, generally using a force plate 106 to measure forces acting on the patient from which the stress on the bone 100 and the device 102 can be determined. The exercises result in the sensor generating power, which correlates to a strain measurement. The measurements are then transmitted from the implanted sensor system, preferably by a corresponding electromagnetic radio signal, to an external receiver 108. The strength of the radio signal and/or the duration of the exercise sequence required to generate the signal yields a measure of the mechanical strain (direct or average) in the fracture-fixation device. The sensor is calibrated such that a known value of generated power corresponds to a given stress or corresponding strain. A record can be kept of the forces exerted upon the fixation device 102 and the corresponding strain measurements determined throughout the healing process by hand or by a computer 110. The extent and rate of the healing in the bone can then be inferred and deduced from analysis of this record. Furthermore, the condition and usefulness of the fracture-fixation device can be monitored and determined with time.

In addition to the periodic assessment of the extent of bone healing through the rigorous monitoring protocol of measuring strain through the exertion of a patient executing dynamic predetermined exercises, continuous everyday monitoring of the fixation device can be accomplished. The strain on the sensing system during day-to-day activities can be monitored by a receiver, such as a radio receiver, housed for example in a wrist watch. Data such as the average and the maximum strain loads experienced by the fixation device can be computed and monitored continuously. These strain measurements can be compared with the predicted allowable strain loads determined during the patients periodic monitoring consultations. During continuous monitoring, the patient can be alerted of bone fixation device overload, for example by the sounding of an alarm on the receiving unit. Preferably, programmable radio receivers that can fit into a wrist watch or other small enclosure that can be worn by a person during the day should be used.

The system and method of using the system operate in the following manner. As the healing of the bone progresses, the amount of strain experienced by the fixation device, and measured by the sensor system, is expected to decrease. Thus, the number of applied loads (i.e., exercise cycles) required to activate the telemetry unit also increases in relation to the extent of healing in a normal sensing operation. One transmission is equivalent to the discrete cumulative strength of the signals. In the direct sensing mode, the strength of the signal produced grows weaker as the bone heals. The healing process can then be plotted as a history of strain in the bone-fixation device.

The combination of periodic monitoring with use of predetermined exercises and continuous day-to-day monitoring of the fixation device, complement each other and provide more information than either method by itself. Thus, the sensing system indicates not only the extent of healing of the fractured bone but also the integrity of the fracture-fixation device itself.

The sensor system of the present invention must be materially and electrically biocompatible, and surgically practical. The sensor element, the electronic components and encasement, the leads connecting the sensor element and the electronic components, and any adhesive between the sensor unit and the fixation device all need to be materially biocompatible. In a preferred embodiment, the sensor is a piezo polyvinylidene fluoride (PVDF) film. PVDF film is a biocompatible material with virtually no tissue reaction. Preferably, any adhesive materials will be either a cyanoacrylate glue or a biomedical grade epoxy. These materials are well-suited for long-term strain measurements and have no adverse biological response. Also, in a preferred embodiment, the leads connecting the sensor element to the electronic circuitry of the buffer unit and telemetry unit are made of a biologically inert metallic material, such as gold or silver.

The electrical biocompatibility of the sensor system is achieved by low electrical power requirements of the sensor element and electrical circuitry. The power requirement of the sensor system is significantly less than 1 mW. This low electrical power requirement is well below the prior art power requirements of 500 mW to 5 watts of power, which have not had adverse reported biological reactions.

Existing surgical techniques are effected minimally by the use of only a few standard electronic components which can be easily miniaturized using available technologies. The electronic components can be miniaturized and thus, leave surgical procedures unaffected by using surface mounted technology or using integrated circuits. Preferably, the maximum size of the electronic circuit without the biocompatible film should not exceed 5 mm by 5 mm and 2 mm thick. The preferred profile thickness of the PVDF film is less than 0.1 mm. This small profile thickness of the sensing system will not interfere with existing surgical procedures.

The sensor element is an active material such as a piezoelectric material that is self-generating with regards to power and voltage. The charge signal generated by the sensor which corresponds to the amount of strain measured by the sensor element can be directly measured by discrete signal monitoring or it can be sent to a buffer unit by way of average signal monitoring. This charge signal is also used to power the telemetry unit. The telemetry unit transmits the charge signal preferably as an electromagnetic radio signal to a receiver outside the body. The telemetry unit can be used to transmit both the discrete and the average charge signal. The sensor system is mounted entirely upon a fracture-fixation device with no extraneous wires or leads. Depending upon placement of the sensing system in a person's body, the telemetry unit may not be required. The sensor element itself produces a signal, which under certain circumstances could be received by a receiving unit without the requirement of the telemetry unit, such as when the receiving unit is close in proximity to the sensing system, which may only be just under the skin.

Although the invention has been shown and described with respect to exemplary embodiments thereof, various other changes, omissions and additions and form and detail thereof, may be made therein without departing from the spirit and scope of the invention.

What is claimed is:

1. An implantable sensing system for a bone fixation device, the system being powered solely by an electric charge generated by the sensing system from a stress imposed upon it, said system comprising:

a strain sensor configured to be affixed on or in a bone fixation device, said sensor configured to monitor and measure strain in the bone fixation device by generating a strain signal in response to stress applied thereupon; and a telemetry unit in communication with said sensor and powered by said strain signal and activated by said sensor upon said strain signal reaching a predetermined value and transmitting said strain signal from said sensor to an external receiver.

2. The sensing system of claim 1, further comprising:

a buffer unit in communication between said sensor and said telemetry unit, said buffer unit capable of collecting and storing said strain signal;

wherein said telemetry unit is activated by said buffer unit upon said stored strain signal reaching a predetermined value and transmitting said stored strain signal from said sensor.

3. The sensing system of claim 1, further comprising:

an external receiving unit in wireless communication with said telemetry unit for receiving said strain signal; and an external processor capable of decoding, analyzing and recording a plurality of said strain signals.

4. The sensing system of claim 1, wherein the self-powered strain sensor is formed of a piezo material.

5. An implantable sensing system powered solely by an electric charge generated from a stress imposed upon it, said system comprising:

a sensor configured to measure strain in a bone fixation device in response to stress imposed upon a bone and the bone fixation device attached thereto;

circuitry in electrical communication with said sensor configured to provide wireless communication of the measured strain to an external receiver.

6. An implantable sensor and telemetry system for monitoring and measuring strain in a fixation device for the purpose of assessing the extent of healing in a bone of a subject, the system comprising:

an implantable sensor unit attached to the fixation device, the sensor unit configured to generate an electric charge in response to stress imposed on the fixation device and relating to the strain measured;

an implantable transmitter powered solely by the charge generated by the sensor unit, the transmitter configured to transmit the charge generated by the sensor unit to an external receiver as a corresponding discrete strain measurement signal; and an external processor capable of processing and analyzing the strain measurement signal for determining the extent of healing in the bone of the subject, whereby the stress imposed upon the fixation device and the charge generated in response to the stress by the sensor unit decreases as the healing in the bone progresses.

7. An implantable sensor and telemetry system for monitoring and measuring strain in a fixation device for the purpose of assessing the extent of healing in a bone of a subject, the system comprising:

an implantable sensor unit attached to the fixation device, the sensor unit configured to generate an electric charge in response to stress imposed on the fixation device and relating to the strain measured;

a buffer configured to collect and store the charge generated by the sensor unit in response to the stress imposed on the fixation device;

an implantable transmitter powered solely by the charge collected and stored by the buffer upon the collected charge reaching a predetermined value, the transmitter configured to transmit the charge collected and stored by the buffer to an external receiver as a corresponding accumulated strain measurement signal; and an external processor capable of processing and analyzing the strain measurement signal for determining the extent of healing in the bone of the subject, whereby the stress imposed upon the fixation device and the charge generated in response to the stress by the sensor unit decreases as the healing in the bone progresses.

* * * * *